United States Patent [19]

Kennedy et al.

[11] Patent Number: 5,616,492

[45] Date of Patent: Apr. 1, 1997

[54] MONOCLONAL ANTIBODIES DIFFERENTIALLY REACTIVE WITH NATIVE AND REDUCTIVELY MODIFIED BOWMAN-BIRK PROTEASE INHIBITOR

[75] Inventors: Ann R. Kennedy, Wynnewood; Cameron J. Koch, Aldan, both of Pa.; Edith M. Lord, Rochester, N.Y.; Xingsheng Wan, Upper Darby, Pa.

[73] Assignees: Trustees of the University of Pennsylvania, Philadelphia, Pa.; University of Rochester, Rochester, N.Y.

[21] Appl. No.: 458,353

[22] Filed: Jun. 2, 1995

Related U.S. Application Data

[62] Division of Ser. No. 358,265, Dec. 19, 1994.

[51] Int. Cl.[6] .............................. C07K 16/00; C12N 5/12
[52] U.S. Cl. .................. 435/341; 530/387.9; 530/388.1; 435/7.93; 435/7.94; 435/7.95; 435/332
[58] Field of Search .............................. 530/388.1, 387.9; 435/7.93, 7.94, 7.95, 240.27

[56] References Cited

U.S. PATENT DOCUMENTS 5,459,044 10/1995 Brandon et al. ..................... 435/7.92

OTHER PUBLICATIONS

Madar, Z. et al. 1979. Comp. Biochem. physiol. 62A: 1057–1061.

*Primary Examiner*—Lila Feisee
*Assistant Examiner*—Minh-Tam B. Davis
*Attorney, Agent, or Firm*—Law Offices of Jane Massey Licata

[57] ABSTRACT

Monoclonal antibodies and a method capable of detecting BBI metabolites in a sample of body fluid or tissue are provided.

4 Claims, No Drawings

MONOCLONAL ANTIBODIES DIFFERENTIALLY REACTIVE WITH NATIVE AND REDUCTIVELY MODIFIED BOWMAN-BIRK PROTEASE INHIBITOR

This is a division of application Ser. No. 08/358,265, filed Dec. 19, 1994.

BACKGROUND OF THE INVENTION

The protease inhibitor, Bowman-Birk protease inhibitor (BBI), is a low molecular weight ($M_r$ 8,000) double-headed inhibitor of trypsin and chymotrypsin isolated from soybeans. It was first discovered approximately forty years ago and has attracted renewed interest from the scientific research community since the discovery of its potent anticarcinogenic effects in several experimental systems. BBI has been shown to prevent or suppress radiation—and chemical carcinogen-induced malignant transformation in vitro and carcinogenesis in mice, rats and hamsters involving several different organs, tissues and cell types. A soybean preparation enriched in BBI, termed BBI concentrate (BBIC), has recently received investigational new drug status from the U.S. Food and Drug Administration and is currently under early phase clinical evaluation as a potential cancer chemopreventive agent.

The distribution and/or metabolic fate of orally administered BBI has been studied in chicks (Madur et al., *Comp. Biochem. Physiol.* 1979, 62A, 1057), rats (Yavelow et al., *Cancer Res.* 1983, 43, 2454) and mice (Persiani et al., *Carcinogenesis* 1991, 12, 1149; Billings et al., *Cancer Lett.* 1992, 62, 191) using radio-iodinated BBI and enzyme inhibition assay as the means to quantitate BBI in tissues and body fluids. In mice, orally gavaged BBI was found to be widely distributed in various organs and tissues within 3 hours of BBI administration, and the bulk of BBI was present in the luminal contents of the small and large bowel, urine and feces (Billings et al., *Cancer Lett.* 1992, 62, 191). While the studies with radioactive BBI have provided important information about the BBI distribution and/or metabolism in these animal models, the same approach is not appropriate for clinical trials due to the concerns about safety and cost. The standard enzyme inhibition assays are not very useful either for measurement of BBI and BBI metabolites in tissue and body fluids since they often do not accurately quantitate specific protease inhibitors, especially in the presence of co-existing protease inhibitors of other types.

High-affinity MAbs to BBI in its native form have been produced by Brandon et al., *J. Agric. Food Chem.* 1989, 37, 1192. One of the two MAbs, named C238, was found to react with a native structure of BBI sensitive to treatment with thiol-reducing agents that disrupt disulfide bridges. Another MAb, designated C217, recognizes a very heat-labile epitope on native BBI molecules (Brandon, D. L., Protease Inhibitors as Cancer Chemopreventive Agents. (1993) Plenum Press, New York, p. 107). C238 antibody, either alone or in combination with C217, can be used in an ELISA to measure nanograms of purified BBI or BBI in processed soybean food products (Brandon et al., *Adv. Exp. Med. Biol.* 1991, 289, 321; Brandon, D. L., *Protease Inhibitors as Cancer Chemopreventive Agents*, Plenum Press, New York, 1993, p. 107); however, neither of these MAbs are capable of detecting BBI metabolites in urine samples collected from humans following oral administration of BBIC. It has been shown, however, in a previous animal study that substantial amounts of orally administered BBI enter the bladder and can be detected in urine (Billings et al., *Cancer Lett.* 1992, 62, 191).

BBI molecules are rich in disulfide content, with each BBI molecule containing 14 cysteine residues that form 7 intramolecular disulfide bridges which maintain the native structure. It is believed that the disulfide bridges on the native BBI molecule are reduced and possibly re-oxidized or alkylated during metabolism in the presence of thiol modifying agents, such as glutathione and other small molecular weight thiols, in tissues and body fluids. The inability of C238 to detect BBI metabolites in human urine samples after BBI administration indicates that at least some of the disulfide bonds on BBI molecules are broken in vivo. It has now been found that immunizing animals with reductively modified BBI results in production of MAbs reactive with BBI metabolites in tissues and body fluids. These MAbs are useful in monitoring exposure levels to BBI during clinical studies.

SUMMARY OF THE INVENTION

An object of the invention is to provide a method of monitoring exposure to BBI in body fluids and tissues which comprises contacting a body fluid or tissue with a monoclonal antibody capable of detecting BBI metabolites in the body fluid or tissue.

Another object of the present invention is to provide monoclonal antibodies capable of detecting BBI metabolites in body fluids and tissues.

Another object of the present invention is to provide a method of producing antibodies capable of detecting and quantitating metabolized protein antigens which comprises immunizing animals with an antigen that has been modified by reduction and re-oxidation.

DETAILED DESCRIPTION OF THE INVENTION

Many proteins in foods and other natural products contain cysteine residues and disulfides that can be reduced and re-oxidized during metabolism. The reduction and re-oxidation of cysteines and disulfides can cause re-arrangement of disulfide bridges within and/or between protein molecules, which will fundamentally alter antigenic structures of the proteins. In the present invention it has been found that immunizing animals with the antigen that has been modified by reduction and re-oxidation, results in the production of antibodies capable of detecting and quantitating the metabolized protein antigens.

Bowman-Birk inhibitor (BBI) is a potent anticarcinogenic agent capable of preventing or suppressing chemical and radiation induced malignant transformation. Studies to evaluate BBI as a human cancer chemopreventive agent have recently begun. It is believed that BBI is reduced and then re-oxidized or alkylated to yield active metabolites in the body, thus making measurement of BBI metabolites an important component in the analysis of therapeutic exposure levels in humans. Small amounts of BBI in its native form can be measured by immunoassay using specific monoclonal antibodies (MAbs); however, the MAbs currently available are not capable of detecting BBI metabolites in human body fluids or tissues. The lack of a sufficiently sensitive method to detect BBI metabolites in body fluids and tissues has been a difficult problem in the clinical trials.

To produce monoclonal antibodies capable of reacting with BBI metabolites, mice were immunized with a BBI antigen radiochemically reduced in formate solution and alkylated with a pentafluorinated derivative of etanidazole (BBI-EF5). The monoclonal antibodies produced by four hybrid cell lines derived from an immunized animal were designated 3B6, 3E3, 4H8 and 5G2 the hybridoma cell lines 5G2, 4H8 and 3E3 being deposited on Aug. 28, 1996 with the American Type Culture Collection, 12301 Parklawn Drive, Rockville, Md., 20852, USA and identified as HB-12178, HB-12179 and HB-12180, respectively. 3B6 and 3E3 were determined to be of IgG1 and IgG2a isotypes while 4H8 and 5G2 are both of IgG2b isotype. All four MAbs contain light chains of κ subtype. Indirect ELISA and inhibitory ELISA experiments were performed using native BBI as antigen to establish that the MAbs were reactive with BBI, and not the chemicals used to modify BBI. In these experiments, it was found that 3B6 reacted well with the native BBI antigen. The binding of 3B6 to BBI immobilized to polystyrene wells was inhibited by BBI pre-mixed with 3B6 antibody in solution. The extent of the inhibition on the binding of 3B6 to immobilized BBI was dependent on the concentration of BBI in solution, indicating that 3B6 reacted with BBI in its native form.

In contrast to 3B6, the MAbs designated 3E3, 4H8 and 5G were found to react very weakly with native BBI, and the binding of these three MAbs to the immobilized BBI could not be inhibited by native BBI. However, in a separate inhibitory ELISA experiment in which reductively modified BBI (BBI-ETAN) was used instead of native BBI, a concentration-dependent inhibition on the binding of 3E3, 4H8 and 5G2 to the modified BBI antigen was achieved.

To confirm that 3E3, 4H8 and 5G2 are reactive with reduced BBI, the binding of these MAbs as well as 3B6 BBI modified with different chemicals was measured. BBI used for these experiments was partially reduced with 720 Gy of radiation in an oxygen-free solution containing 100 mM formate (BBI-RR) or extensively reduced with 100 mM dithiothreitol (BBI-DTT), and the BBI partially reduced with radiation was re-oxidized with 5,5'-dithiobis-(2-nitrobenzoic acid) (BBI-DTNB) or alkylated with N-ethylmaleimide (BBI-NEM). BSA was treated the same ways and served as a negative control. The BBI and BSA so treated were attached to microwell plates as the antigens for ELISA experiments. As previously indicated, 3B6 reacted well with native BBI. Partial reduction of BBI with radiation in formate solution increased the binding of 3B6 to BBI by 57%. Subsequent treatments of BBI with DTNB or NEM reversed the enhancing effect of radiation and formate on the antigenic reactivity of BBI with 3B6. Extensive reduction of BBI with DTT completely abolished the reactivity of BBI with 3B6. In contrast to 3B6, the other three MAbs were not highly reactive with BBI in its native form. Partial reduction of BBI with radiation in formate solution significantly increased the binding of 4H8 and 5G2 to the BBI antigen. Re-oxidation of the reduced BBI with DTNB decreased the binding of 4H8 and 5G2 to the modified BBI by 36% and 29%, respectively. Alkylation of the reduced BBI with NEM further increased the binding of 4H8 and 5G2 to the modified BBI by 37 to 38%. Treatment of BBI with DTT was more effective than the radiochemical reduction in promoting the binding of 5G2 to BBI but less effective than radiochemical reduction in enhancing the binding of 4H8 to BBI. The reactivity of 3E3 with BBI in different treatments was too low to allow a significant comparison; however, the general pattern of 3E3 binding to BBI of different treatments was similar to that of 5G2. None of the four MAbs reacted with BSA following any of these treatments. These results indicate that the epitope recognized by 3B6 is maintained by disulfide bridge(s) that are sensitive to treatment with DTT. In contrast, 3E3, 4H8 and 5G2 react with epitopes on BBI molecules that had been reductively modified. None of these MAbs react with the chemicals used to modify the BBI antigen since they did not show any noticeable reactivity with BSA modified by the same treatments.

3E3, 4H8 and 5G2 all react with reductively modified BBI. To determine whether these MAbs recognize different epitopes on the reduced BBI molecules, a competition ELISA was performed in which constant amounts of 4H8 or 5G2 antibodies were mixed with varying amounts of 3E3 antibody and the antibody mixtures were applied to polystyrene wells coated with reductively modified BBI antigen (BBI-ETAN). 4H8 and 5G2 were also mixed with varying amounts of 3B6 and included in the experiment as controls. The bindings of 4H8 and 5G2 to the immobilized BBI antigen in the presence of 3B6 or 3E3 competitor antibodies were detected by a secondary antibody specific for mouse IgG2b immunoglobulins, which detects 4H8 and 5G2 but not 3B6 or 3E3. The results showed that the bindings of both 4H8 and 5G2 to the modified BBI antigen were inhibited by 3E3 in a dose-dependent fashion. The bindings of 4H8 and 5G2 to BBI were not inhibited by 3B6 even when the concentration of 3B6 antibody was approximately 100 times that of 4H8 or 5G2 in the reaction mixture. Since the binding 3E3 to BBI prevented 4H8 and 5G2 from reacting with the BBI antigen, the epitope recognized by 3E3 is probably located close to the epitopes recognized by 4H8 and 5G2. 3E3 competed with 4H8 and 5G2 for binding sites on BBI molecules with nearly identical efficiencies as represented by the slopes of the inhibition curves. It is likely that the epitopes recognized by 4H8 and 5G2 are also located close to each other on the reduced BBI molecules.

To further establish that the epitope(s) recognized by 3E3, 4H8 and 5G2 are clustered in a small region on the reduced BBI molecules, sandwich ELISA experiments were performed using 4H8 and 5G2 as capture antibodies and 3E3 as detection antibody. The binding of 3E3 to the BBI molecules captured by 4H8 and 5G2 was measured with a secondary antibody specific for mouse IgG2a immunoglobulins, which detects 3E3 but not 4H8 or 5G2. In these experiments, 3E3 did not bind to BBI captured by either 4H8 or 5G2 on polystyrene wells, suggesting that the binding of either 4H8 or 5G2 effectively blocked the access of 3E3 to its binding site on the reduced BBI molecules. This suggests that the epitopes recognized by 3E3, 4H8 and 5G2 are all present near one another on the reduced BBI molecules.

Reduction of BBI with γ-radiation in formate solution substantially increased the antigenic reactivity of BBI with 4H8 and 5G2. Re-oxidation with DTNB partially reversed the effect of radiation and formate while alkylation with NEM further enhanced the antigenic reactivity of BBI-RR with 3E3, 4H8 and 5G2. These findings suggest that 3E3, 4H8 and 5G2 recognize epitopes that are exposed only when some of the disulfides of BBI molecules are reduced and the native three dimensional structure of BBI is relaxed. Re-oxidation of the free sulfhydryl groups resulted from the reduction of disulfides to form new disulfide bonds may restore the native three dimensional structure of BBI and seal off some of the epitopes recognized by 3E3, 4H8 and 5G2. However, the restoration of the three dimensional structure and concomitant sealing off of the epitopes may not be complete, since the newly formed disulfide bonds may link cysteine residues that are not normally paired in native BBI molecules. This may explain the partial effect of DTNB in reversing the enhancement of BBI antigenic reactivity with 3E3, 4H8 and 5G2 by γ-radiation in formate solution. Alkylation of the free sulfhydryl groups resulting from the reduction of disulfides will prevent spontaneous re-oxidation of the sulfhydryl groups, thereby stabilizing the epitopes recognized by 3E3, 4H8 and 5G2.

The ability of 3E3, 4H8 and 5G2 to detect BBI metabolites in urine suggests that the metabolism of BBI in vivo may involve the reduction of disulfide bonds. The molecular weights of BBI metabolites were significantly higher than BBI monomer, as demonstrated by Western blot analysis, indicating that the reduced BBI is combined with certain types of proteins in vivo. The reduced BBI and its target proteins are probably connected via covalent bond(s) which sustained 10-minute heating at 85° C. in the presence of 1% β-mercaptoethanol. The appearance of the BBI metabolites as distinctive bands in the Western blot analysis suggests that there may be favored target proteins for BBI or BBI metabolites.

The antibodies of the present invention can be used to monitor exposure to BBI through the detection of BBI metabolites in a body fluid or tissue. By "body fluids" it is meant to include, but is not limited to, urine, blood, serum, plasma, saliva, cerebrospinal fluid, and bile. In a preferred embodiment, an antibody selected from a group consisting of 3E3, 4H8 and 5G2 is used to measure metabolites in urine. By "tissue" it is meant to include, but is not limited to, epithelium, connective tissue, muscle tissue and nerve tissue. In a preferred embodiment, an antibody selected from a group consisting of 3E3, 4H8 and 5G2 can be used to measure metabolites in epithelial cells. As used herein, the term "antibody" is meant to refer to complete, intact antibodies, Fab fragments and F(ab)$_2$ fragments. In this method, an antibody raised in an animal immunized with the BBI antigen that had been modified by reduction and re-oxidation, is contacted with a body fluid or tissue, preferably urine or epithelial cells, respectively, in a standard immunoassay procedure such as an ELISA.

For example, a BBI containing preparation was administered orally to normal healthy volunteers and urine samples were collected before and after administration of the preparation. The BBI metabolites were detected by the inhibitory ELISA method using 5G2 as the primary antibody. The results showed that the urine samples collected from 1 through 14 hours after administration contained varying amounts of substances reactive with 5G2, presumably BBI metabolites. The amount of BBI metabolites in the urine sample collected 24 hours after BBI administration was barely detectable. To identify BBI metabolites, concentrated urine samples were electrophoresed on SDS-polyacrylamide gels, transferred to nitrocellulose membrane and detected by immuno-peroxidase staining using the four MAbs. On the nitrocellulose membrane stained with 4H8, the BBI standard appeared as a broad band with an apparent molecular weight (estimated from the center of the band) of 8 kd, which agrees well with reported molecular weight of BBI monomer. The radiochemically modified BBI was stained as a smear run throughout the lane. The BBI metabolites appeared as a major band and a minor band of approximately 73 kd and 133 kd, respectively. The patterns of the immuno-peroxidase staining with 3E3 and 5G were nearly identical to those obtained with 4H8, whereas 3B6 did not stain even the BBI standard under the reducing condition as expected. The apparent molecular weight of the BBI metabolite was significantly higher than BBI monomer even after the urine sample was heated in the presence of 1% β-mercaptoethanol, suggesting that the metabolized BBI was covalently bound to certain proteins. Since 3E3, 4H8 and 5G2 could detec the BBI metabolite in urine, they will be useful reagents for monitoring BBI exposure and clearnace in clinical chemoprevention trials.

The techniques involved in carrying out immunoassays such as an inhibitory ELISA are well-known to those of skill in the art. The use of the antibodies of the present invention in such assays will become routine to those of skill in the art upon this disclosure.

The following examples are provided for illustrative purposes only and are not intended to limit the invention.

EXAMPLES

Example 1: Antigen Preparation, Immunization and Cell Fusion

Purified BBI used in the present study was purchased from Sigma Chemical Company (St. Louis, Mo.). To prepare antigen for animal immunization, BBI was reduced with γ-radiation in formate solution and re-oxidized with EF5 by a radiochemical method as previously described (Koch and Raleigh, *Arch. Biochem. Biophys.* 1991, 287, 75; Lord et al., *Cancer Res.* 1993, 53, 5721). The modified BBI antigen was emulsified with Freund's complete adjuvant and injected i.p. and i.m. to immunize C57Br/cdj X SJL/Br-H-2 (k) mice. The details of the immunization and cell fusion have been reported previously (Lord et al., *Cancer Res.* 1993, 53, 5721). The fusion products were bulk-cultured in a roller bottle for 2 days, re-suspended in 10 ml medium and frozen in liquid nitrogen in 1 ml aliquots.

To minimize the chance of selecting MAbs reactive with the chemicals used for modifying BBI antigen and to characterize the epitopes recognized by the resultant MAbs, BBI in its native form or modified to BBI-RR, BBI-ETAN, BBI-EF5, BBI-DTNB, BBI-NEM or MMI-DTT were used as antigens for antibody screening and immunological assays as specified in the following examples.

To modify the native form of BBI to BBI-RR, wherein some disulfide bonds are reduced to —SH groups and the native form is disrupted, 5 mg/ml of BBI was dissolved in 100 mM formate buffer. This solution was deoxygenated and irradiated to 720 Gy.

To modify the native form of BBI to BBI-ETAN or BBI-EF5, wherein some of the protein —SH groups form 2-nitroimidazole adducts, thus making the native structure impossible, BBI-RR was mixed with 10 mM ETAN or EF5 at a ratio of 1:20. The mixture was then deoxygenated and irradiated to 2000 Gy.

To modify the native form of BBI to BBI-DTNB, wherein the protein —SH groups are re-oxidized by DTNB, thus making the native configuration unlikely but allowing for the formation of aggregates, BBI-RR was mixed with 1.25 mM DTNB at a ratio of 1:4. The mixture was then incubated at room temperature for 30 minutes prior to use.

To modify the native form of BBI to BBI-NEM, wherein the protein —SH groups are alkylated with NEM making formation of the native structure impossible, BBI-RR was mixed with 5.0 mM NEM at a ratio of 4:1. The mixture was then incubated at room temperature for 30 minutes.

To modify the native form of BBI to BBI-DTT, wherein the disulfides are reduced to —SH groups thus disrupting the native structure, 5 mg/ml of BBI was dissolved in formate buffer. This solution was then mixed with 100 mM DTT solution at a ratio of 1:4.

Bovine serum albumin (BSA) was treated similarly and included in the assays as a negative control.

Example 2: Screening, Cloning and Antibody Preparation

To screen for hybrid cells that produce antibodies against BBI, one tenth of the frozen cell fusion products was thawed and diluted into 50 ml of hybridoma culture medium (Sigma Chemical Co., St. Louis, Mo.) supplemented with 20% fetal bovine serum (FBS), 50 μM hypoxanthine, 0.4 μM aminopterin and 8 μM thymidine, and cultured in five 96-well tissue culture plates for 5 days at 37° C. in an atmosphere consisting of 8% CO$_2$ and 92% air. Two drops of hybridoma culture medium without aminopterin were added to each weel on day 5 and 9. After two weeks of incubation, 100 μl of medium was transferred from each well to 96-well plates coated with BBI (100 ng per well) and screened by indirect ELISA for antibody production. The cells that produced antibodies to BBI were cloned by the limiting dilution method, expanded and frozen in liquid nitrogen in 1 ml aliquots.

The subtypes of the light and heavy chains of each MAb were determined using a MAb-based isotyping system (Gibco BRL, Gaithersburg, Md.) according to the manufacturer's instructions and confirmed by the indirect ELISA method using goat antibodies against mouse immunoglobulins of specific isotypes. Selected hybridoma clones were expanded in hybridoma culture medium supplemented with 20% FBS. MAbs were prepared from the hybridoma culture supernatants by ammonium sulfate precipitation, dialyzed against three changes of phosphate buffered saline (pH 7.0) at 4° C., reconstituted to 1/10 volume of the hybridoma culture supernatants and stored in aliquots at −20° C. before use.

Example 3: BBI Administration

A BBI containing preparation having 400 chymotrypsin inhibitor (C.I.) units was administered orally to healthy volunteers in a single dose. Urine samples were collected immediately before and 1, 3, 6, 9, 14 and 24 hours after administration of the preparation and stored in aliquots at −20° C. before use.

Example 4: Enzyme Linked Immunosorbant Assays

To prepare polystyrene plates coated with BBI antigen for ELISA experiments, purified BBI and BBI modified by different treatments were diluted to 1 μg per ml in 10 mM phosphate buffer (PB; pH 7.0), added to 96-well plates at 100 μl per well and incubated at room temperature for a minimum of one hour or at 4° C. overnight for BBI to attach. After removal of the BBI solution, the plates were fixed with 100 μl per well of 0.1% glutaraldehyde for 10 minutes at room temperature, washed once with PB and incubated with 100 μl per well of 0.1 M glycine for 5 minutes to block fee aldehyde groups. The plates were then washed once with PB, incubated with 150 μl per well of 0.5% BSA in phosphate buffer (BSA-PB) for 1 hour to saturate non-specific binding sites. The prepared plates were used immediately or stored at −20° C. before use.

For indirect ELISA experiments, 100 μl of MAb diluted to specified concentrations in BSA-PB was added to each well of the 96-well plates coated with BBI and incubated at 38° C. for 1 hour. The bound MAbs were detected with β-galactosidase (BGAL) or horseradish peroxidase (HRP) conjugated goat anti-mouse immunoglobulins (Southern Biotechnology Associates, Birmingham, Ala. The BGAL activity in each well was assayed in 100 μl of 40 mM boric acid-borax buffer (pH 8.5) containing 15 mg/ml of o-nitrophenyl-β-D-galactopyranoside (ONG) substrate (Sigma Chemical Co., St. Louis, Mo.). The absorbance was measured at 415 nm with a microplate reader (Model 7250, Cambridge Techology, Watertown, Mass.) after 1 hour of incubation at 37° C. The HRP activity in each well was assayed in 100 μl of 3,3',5,5'-tetramethylbenzidine (TMB) substrate solution prepared from TMB tablets (Sigma Chemical Co., St. Louis, Mo.) according to the manufacturer's instruction, and the absorbance was measured at 650 nm after 15 minutes of incubation at room temperature.

Sandwich ELISA experiments were performed by first coating the 96-well plates with an appropriate capture MAb (10 μg per ml in PB, 100 μl per well) overnight at 4° C. After removal of the capture MAb solution and blocking with 150 μl per well of BSA-PB for 1 hour, 100 μl of BBI or urine samples was applied to each well and incubated at 37° C. for 1 hour. BBI retained on the 96-well plates by the capture MAb was assayed with a detection MAb that is different from the capture MAb in isotypes. The binding of the detection MAb to BBI was quantitated with HRP-conjugated goat antibodies specific for the isotype of the detection MAb and the HRP activity was determined as described above.

In inhibitory ELISA, MAb was pre-incubated at 37° C. for 30 minutes with appropriately diluted BBI or urine samples. The incubated solution was added 100 μl per well to 96-well plates coated with BBI and incubated at 37° C. for 1 hour. The binding of the MAb to BBI fixed on polystyrene wells was quantitated as described for indirect ELISA. The MAb pre-incubated in PB without BBI were included in the experiments as control. The results of inhibitory ELISA were expressed as % inhibition, which was calculated as follows: $(A_{control} - A_{test})/A_{control} \times 100\%$. In competition ELISA, The MAb to be tested was first mixed with varying amounts of a competitor MAb of a different isotype. The MAb mixture was added at 100 μl per well to 96-well plates coated with BBI and incubated at 37° C. for 1 hour. The binding of the test MAb to BBI was measured with HRP-conjugated goat antibodies specific for the isotype of the test MAb. The HRP activity in each well was quantitated as described above.

Example 5: Western Blot Detection of BBI and BBI Metabolites in Urine

To concentrate BBI metabolites for Western blot analysis, urine samples were processed by one of the two methods. In the first method, a pooled urine sample collected from a female volunteer in a 24-hour period after administration of a BBI containing preparation was dialyzed against $H_2O$ overnight to remove salts. The dialyzed urine was lyophilized and reconstituted in $H_2O$ as a 1% (w/v) solution. In the second method, 500 μl urine samples collected from a male volunteer at 14 or 24 hours after administration of a BBI containing preparation was dried in a SpeedVac concentrator (Savant, Farmingdale, N.Y.) and reconstituted in 100 μl of $H_2O$. Twenty μl of the reconstituted urine was mixed with 5 μl sample buffer containing 5% β-mercaptoethanol, heated for 10 minutes at 85° C. and electrophoresed on 8% SDS polyacrylamide slab gels. The proteins were then electrophoretically transferred onto Immobilon-N membrane (Millipore Corp., Bedford, Mass.). The membrane was blocked for 30 minutes in 0.5% BSA-PB, then incubated for one hour with an MAb diluted 1:100 in BSA-PB. After three rinses with PB, the membrane was incubated for one hour with HRP-conjugated goat anti-mouse IgG diluted 1:500 in BSA-PB. The membrane was stained for 15 minutes in 3,3'-diaminobenzidine tetrahydrochloride (DAB) substrate solution prepared from DAB tablets (Sigma Chemical Co., St. Louis, Mo.) according to the manufacturer's instruction.

What is claimed:

1. A monoclonal antibody which is selected from a group consisting of 3E3, 4H8 and 5G2, and is capable of detecting metabolites of Bowman-Birk protease inhibitor in a body fluid or tissue, said antibodies produced by hybidoma cell lines with ATCC designation number HB-12180, HB-12179, and HB-12178, respectively.

2. A hybridoma cell line producing monoclonal antibody 3E3, and having ATCC designation number HB-12180.

3. A hybridoma cell line producing monoclonal antibody 4H8, and having ATCC designation number HB-12179.

4. A hybridoma cell line producing monoclonal antibody 5G2, and having ATCC designation number HB-12178.

* * * * *

UNITED STATES PATENT AND TRADEMARK OFFICE
CERTIFICATE OF CORRECTION

PATENT NO. : 5,616,492

DATED : April 1, 1997

INVENTOR(S) : Kennedy et al.

It is certified that error appears in the above-indentified patent and that said Letters Patent is hereby corrected as shown below:

At col 5, line 52, please delete "detec" and insert therefor --detect--.

At col 6, line 56, please delete "weel" and insert therefor --well--.

Signed and Sealed this

Sixteenth Day of December, 1997

*Attest:*

BRUCE LEHMAN

*Attesting Officer*     *Commissioner of Patents and Trademarks*